(12) United States Patent
Tchirikov (10) Patent No.: US 11,484,026 B2
(45) Date of Patent: Nov. 1, 2022

(54) ARTIFICIAL WOMB SYSTEM AND PLACENTA

(71) Applicant: UNIVERSITÄTSKLINIKUM HALLE (SAALE), Halle (DE)

(72) Inventor: Michael Tchirikov, Halle (DE)

(*) Notice: Subject to any disclaimer, the term of this patent is extended or adjusted under 35 U.S.C. 154(b) by 0 days.

(21) Appl. No.: 16/496,233

(22) PCT Filed: Apr. 3, 2017

(86) PCT No.: PCT/EP2017/057829
§ 371 (c)(1),
(2) Date: Nov. 27, 2019

(87) PCT Pub. No.: WO2018/171905
PCT Pub. Date: Sep. 27, 2018

(65) Prior Publication Data
US 2020/0323197 A1    Oct. 15, 2020

(30) Foreign Application Priority Data
Mar. 21, 2017  (WO) .................. PCT/EP2017/056704

(51) Int. Cl.
*A01N 1/02*         (2006.01)
*A61G 10/02*        (2006.01)
(Continued)

(52) U.S. Cl.
CPC ........... *A01N 1/0247* (2013.01); *A61G 10/02* (2013.01); *A61G 11/00* (2013.01); *A61M 1/3621* (2013.01);
(Continued)

(58) Field of Classification Search
CPC ...... A61M 1/3621–367; A61M 1/1698; A61M 2202/0494; A61M 2210/1466;
(Continued)

(56) References Cited

U.S. PATENT DOCUMENTS 5,207,639 A   5/1993  Cooper
5,218,958 A   6/1993  Cooper
(Continued)

FOREIGN PATENT DOCUMENTS

DE  202014103422 U1  9/2014
WO  WO2007008840     1/2007
(Continued)

OTHER PUBLICATIONS

Younge, N. et al, "Survival and neurodevelopmental outcomes among periviable infants", The New England Journal of Medicine, vol. 376, No. 7, pp. 617-628, (Feb. 16, 2017).

*Primary Examiner* — Thaddeus B Cox
(74) *Attorney, Agent, or Firm* — McHale & Slavin, P.A.

(57) ABSTRACT

The invention relates to an artificial womb system for supporting newborns, in particular extremely premature infants between the 21/0 and 28/0 week of pregnancy, comprising the following: a chamber (1) of the artificial womb, said chamber being formed by an at least partially ultrasound-permeable wall (2) and comprising a lumen (14) for maintaining a physiologically intraamnial pressure and for receiving the artificial amniotic fluid (15) and a newborn or a premature infant, at least one access for supplying the premature infant in the artificial womb with nutrients, a dialysis device (9), and an oxygenator (8) and/or a gassing device for supplying oxygen to the newborn or premature infant, wherein means are provided in order to maintain an intraamnial pressure of >0 mBar in the chamber (1) of the artificial womb, said pressure acting on the newborn, in addition to the atmospheric pressure.

18 Claims, 3 Drawing Sheets

(51) Int. Cl.
*A61G 11/00* (2006.01)
*A61M 1/36* (2006.01)

(52) U.S. Cl.
CPC ............ *A61M 2202/0007* (2013.01); *A61M 2202/0494* (2013.01); *A61M 2210/1466* (2013.01); *A61M 2240/00* (2013.01)

(58) Field of Classification Search
CPC ...... A61G 10/00–04; A61G 11/00–009; A01N 1/0247
See application file for complete search history.

(56) References Cited

U.S. PATENT DOCUMENTS

| | | | |
|---|---|---|---|
| 2004/0193096 A1* | 9/2004 | Cooper | A61G 11/00 604/19 |
| 2007/0010005 A1* | 1/2007 | Sitzmann | A61G 11/00 435/283.1 |
| 2013/0316980 A1* | 11/2013 | Tchirikov | A61P 43/00 514/78 |
| 2014/0255253 A1 | 9/2014 | Fusch et al. | |
| 2016/0317117 A1* | 11/2016 | Mason | A61B 7/04 |
| 2017/0128322 A1* | 5/2017 | Fassihi | A61H 33/6068 |

FOREIGN PATENT DOCUMENTS

| | | |
|---|---|---|
| WO | WO2012093087 | 7/2012 |
| WO | WO2014145494 | 9/2014 |
| WO | WO2016154319 | 9/2016 |
| WO | WO2016205622 | 12/2016 |
| WO | WO2018171905 | 9/2018 |

* cited by examiner

ARTIFICIAL WOMB SYSTEM AND PLACENTA

CROSS REFERENCE TO RELATED APPLICATIONS

This is a national stage filing in accordance with 35 U.S.C. § 371 of PCT/EP2017/057829, filed Apr. 3, 2017, which claims the benefit of the priority of European Patent Application No. PCT/EP2017/056704, filed Mar. 21, 2017, the contents of each are incorporated herein by reference.

TECHNICAL AREA

Premature infants born prior to the $24^{th}$ week of gestation (WG) weighing less than 500 g without a sign of life are considered "late-onset" and are not recorded statistically as births. Worldwide, this relates to millions of children in the developed countries. Of all extremely premature infants (i.e. before 28th week of gestation) 40% die within the first five years (WAO Report "Born to Soon," 2011). 91% of premature infants die in the 23rd week of gestation and 67% in the 24th week of gestation (Stoll et al., JAMA 2015). Extremely premature infants rarely survive without serious long-term consequences (Chen F. et al., Arch Dis Chld Fetal Noanatal 2016; 101:377-83). Only 6% of premature infants in the 22nd WG survive until discharge from hospital, with 95% to 96% of them showing significant physical and/or mental damage (Stoll et al., JAMA 2015). At 22 weeks of gestation, 89% of the surviving premature infants show a retinopathy with a severity >3. In the 23rd week of gestation, 42% are affected. Only a percentage of <20% of premature infants survives until discharge from the hospital without necrotizing enterocolitis, sepsis, meningitis, bronchiopulmonary hypoplasia and/or marked cerebral hemorrhage in premature infants under the 24th week of gestation (Stoll et al., JAMA 2015). A similar picture with sometimes drastically poor survival rates is also provided by a recent study in newborns between the 22nd and 24th week of pregnancy (Noelle Younge et al., Survival and Neurodevelopmental Outcomes of Periviable Infants, The New England Journal of Medicine, Feb. 16, 2017 vol. 376 no. 7).

STATE OF THE ART

To counteract this problem, methods and therapies are being developed to increase the survival rate of extremely premature infants and to reduce late effects or premature deaths. One approach is to put the premature infants into a neonatal-incubator after childbirth to provide an "artificial" womb. This way, multiple placenta functions of the womb may be replaced as completely as possible, at least temporarily. The aim is not only to increase the survival rate, but also to avoid lasting serious complications due to the fetal programming in extremely premature infants.

The human placenta is a complicated fetal organ that, on the one hand, performs an important supply function for the embryo or fetus. This includes, for example, a transplacental active and/or passive transport of oxygen, amino acids, fatty acids, microelements, vitamins, water, electrolytes, growth factors, hormones, cytokines and other regulatory substances (NO etc.). In part, substances such as amino acids, hormones, NO are also synthesized in the placenta itself. Since the fetal kidneys "in utero" do not yet have a disposal function, they produce a diluted hypoosmotic alkaline fluid, which represents the main part of the total amniotic fluid. A fetus drinks about 250 to 300 ml/kg amniotic fluid daily (Gilbert W M and Brace R A. Semin Perinatol. 1993). Disposal of the fetal metabolites such as bilirubin or $CO_2$ occurs via the placenta. Thereafter, the maternal kidneys and lungs take over the disposal function.

The placenta also provides an important barrier to maternal bacteria and viruses to keep them away from the developing child. Only the IgG antibodies are able to cross the placental barrier.

The amnion, which already encloses the embryo with its umbilical cord from the 4.-5. WG, consists of 2 membranes, namely of the amniotic and chorionic membranes. Their function is mainly to separate the fetus and the uterus (Benirschke et al., Pathology of the Human Placenta, Springer Verlag, 2012).

Cytokines and prostaglandins are synthesized in the amniotic membrane which also plays a role in the production of amniotic fluid. The amniotic fluid is also involved in the direct transmission of maternal sounds, such as heartbeat, breathing, intestinal sounds, but also of the maternal voice, directly to the ear of the fetus.

Artificial life support systems, neonatal incubators or artificial wombs are known. For example, U.S. Pat. No. 5,218,958 describes a life support system for a premature infant which is embedded in the natural maternal placenta via the umbilical cord. The system comprises upper and lower chambers, which are separated by a vault-like partition. The lower chamber contains physiological fluid in which the premature infant is placed, while the upper chamber has an oxygen-containing atmosphere and nutrient accesses to provide the placenta with nutrients. In this system, the most basic physiological care of the premature infant is facilitated.

WO 2012/093087 A1 describes an aqueous composition with a reduced chloride content, which can be used as an amniotic fluid substitute. The structure of a life support system for premature infants or an artificial womb is not described.

The US 2014/0255253 A1 describes an artificial womb, which is equipped with an oxygen supply system for the premature infant. The device comprises a gas permeable membrane and a vascular network which enables, for example, the delivery of fluids containing nutrients. The oxygen supply takes place via an oxygenator via the umbilical cord using an umbilical catheter (umbilical cord catheter) comprising a venous catheter and an arterial catheter. Via this catheter system a gas mixture of 40% oxygen in nitrogen was administered. The security of the catheter or its exact structure is not described.

Another possibility of oxygenation of a premature infant is described by WO 2014/145494 A1, in which the circulatory system of the premature infant is coupled to an extracorporeal membrane, which is part of an oxygen supply system. A variant provides that the oxygenator is enriched with fetal blood. The incubation chamber comprises a sterile liquid and may be warmed up as needed. In the system, it is provided that the premature infant is placed in the incubation chamber and fed intravenously. Further, the incubation chamber provides inlets and outlets as well as a pump with at least one filter, if required. The risk of infection and the risk of developing sepsis are very high.

DE 20 2014 103 422 U1 describes a womb emulating incubator having a lumen for accommodating a newborn and an environmental change system configured to alter at least one parameter in a predetermined time cycle to replicate the human intrauterine environment. These include, for example, a light filter, a noise damper, a shock absorber. Furthermore, parameters may also be generated, including, for example, a lighting system, an odor system, a noise system, or a motion system. The physiological requirements of an extremely premature infant embedded in a womb are not addressed. Rather, it is about providing a consistent, safe and peaceful environment for a newborn.

WO 2016/154319 A1 describes an artificial womb and method for the production thereof, in which microfluidic channels are provided, which are arranged between a membrane in such a way that a fluid transport can take place through the membrane. Furthermore, cell layers of at least two different cell types are provided, which adhere to the two sides of the membrane. The first cell type comprises for example, primary human placental villous endothelial cells, while the second cell type comprises choriocarcinoma cells.

The womb systems described in the prior art are insufficient in many respects, on the one hand, because they do not provide physiologically equivalent conditions or because the treatment of the extremely premature infants is inappropriate.

Thus, U.S. Pat. No. 5,218,958 describes a physiological solution in which the tissue of the placenta swells within 24 hours, paralyzing the function completely. The described solution is unsuitable for the child and his life-preservation, also because the proportion of Na+ and Cl-ions is too high. Also, the concept assumes that the placenta is connected to the umbilical cord. The reuse of a detached placenta for the care of the premature infant has not been successful in practice. Premature placental detachment leads to an intrauterine fetal death. After the detachment, the placenta contracts and loses its function. After birth, on the other hand, several fissures develop in the placenta, leading to continuous blood loss in the premature infant.

The amniotic fluid substitutes described in WO 2014/145494 A1 are unsuitable because of too low a pH-value, increased osmolarity, the absence of microelements, glucose and an insufficient NaCl-concentration.

Extracorporeal membrane oxygenation (ECMO), which is usually veno-venous, is often used to replace lung function. In addition, extracorporeal life support (ECLS) systems are also available that allow extracorporeal oxygenation and $CO_2$ elimination, thereby replacing lung function. With the ECLS also a hemodynamic relief of the heart is possible, since it provides circulatory support. The ECMO systems differentiate between veno-arterial ECLS and veno-venous ECMO. The blood is delivered from the venous system of the patient by means of a pump and after passage through the oxygenator it is fed back into the arterial system. The oxygenation of the organism is composed of the ECMO/ECLS flow and the remaining circulatory function of the patient. The connection to the extracorporeal circuit is usually enabled via cannulas. In neonates and infants, the cervical vessels (i.e. the carotid artery or the jugular artery) are often used for cannulation because they have the largest diameter. However, this could lead to irreversible damage due to a low arterial perfusion of the brain.

Presentation of the Invention

Against this background, it is the object of the present invention to provide an improved neonatal life support system, in particular for extremely premature infants born between the 21/0 and 28/0 week of gestation, which can increase the overall life expectancy of the premature infant.

This object is achieved by an artificial womb system and a method for ex vivo treatment of a newborn or premature infant, as claimed in the following claims.

Preferred embodiments are described in the subclaims.

The artificial womb system (uterine system) of the present invention is used to support the life of newborn infants who would not be viable without assistance, especially extremely premature infants between the 21/0 and 28/0 WG (x/y WG=gestational week/day), i.e. preferably of premature infants born before the 28th week of gestation. The womb system initially comprises an artificial womb formed by an at least partially ultrasound-permeable wall, with a lumen for holding amniotic fluid and a premature infant. By using an ultrasound-transmitting material for the wall of the artificial womb chamber, ultrasound measurements are possible, which are preferably performed with probes within a frequency range of 1 to 15 MHz, preferably within a frequency range of 3.5 to 12 MHz or its sub-ranges. Preferred materials for the wall of the artificial womb chamber are therefore transparent plastics or other ultrasound-permeable materials. In a preferred variant, the wall is also translucent. Preferably, the wall consists of a material which is either colored itself shading the interior or acting light-repellent upon incidence of light.

The system also includes at least one access to provide the premature infant in the artificial womb chamber with amniotic fluid. Preferably, nutrients, hormones, growth factors or other vital substances and compounds are dissolved in the amniotic fluid.

Since the kidney function of the newborn or extremely premature infant is not yet developed, a dialysis device is also provided to dispose of the metabolic waste products of the premature infant. An oxygenator and/or a gassing device provides the oxygen supply for the premature infant, either with oxygen, with an oxygen-containing gas mixture or with Carbogen®.

The inventor of the present invention has found that the devices and methods described in the prior art are actually inadequate, because they do not take into account the intraamnial pressure of the womb. According to the invention, it is therefore provided that means are provided in order to maintain an intraamnial pressure of >0 mbar affecting the newborn in the artificial womb chamber in addition to the atmospheric pressure. Preferably, in the artificial womb chamber, a pressure between 2 mbar and 1000 mbar, preferably between 5 mbar and 600 mbar, preferably between 5 mbar and 100 mbar, or areas in between, in addition to atmospheric pressure is maintained to affect the newborn. The atmospheric pressure usually is 1 bar (about 1013 hPa). The absolute pressure in the artificial womb is therefore preferably up to 2 bars or any value in between. Alternatively, it is also possible to apply an absolute pressure of 5 mbar to 2 bar. Also intermediate ranges or intermediate values of the above mentioned ranges are comprised by the invention. In order to maintain the intraamnial pressure, facilities or means are provided, such as a pump or a pressurized container filled with artificial amniotic fluid or an oxygen mixture.

In a preferred version, according to the invention, the intraamnial pressure maintenance in the artificial womb is accomplished by providing a pump for the transport and/or oxygenation of the amniotic fluid. This pumps amniotic fluid, Carbogen® or an oxygen-containing mixture into the artificial womb chamber. Alternatively, a pressurized container (e.g. filled with amniotic fluid or an oxygen mixture) may also be used to establish the desired intraamnial pressure in the artificial womb. Building up of the required pressure which acts on the neonatal can also be realized by a fluid column, for example by amniotic fluid which acts on the newborn filled into the artificial womb chamber and building up a pressure of >0 mbar, preferably between >0 mbar and 1 bar, in addition to the atmospheric pressure (1 bar). Alternatively, the pressure build-up in the artificial womb chamber can also take place via gassing. Depending on which means are selected for the intraamnial pressure build-up, the chamber may be closed or open at least on one side. An open chamber (preferably upwards) would be conceivable, for example, when using (amniotic) fluid, in which the newborn is embedded.

In a preferred embodiment, it is provided that the oxygenator and the dialysis device are connected to a port system, which in turn is connected to the umbilical cord of the premature infant. The port system according to the invention consists of at least two catheters for connecting the umbilical vein and at least one umbilical artery of the premature infant. Preferably, the port system according to the invention comprises a catheter for the umbilical vein and two catheters for the two umbilical arteries. Furthermore, a stent connected to the catheters is provided, via which the port system is anchored to the umbilical cord.

The inventor has also recognized that the best physiological access to the extremely premature infant's cardio-circulatory system is the umbilical cord. The problem is that the umbilical cord falls off shortly after birth, usually within 3 to 4 days. Thus, it seems to be impossible to make long-term use of the umbilical cord to provide the premature infant. On the other hand, permanent catheterization of the intrahepatic umbilical vein via the navel is associated with a significant risk of developing premature infant omphalitis or sepsis.

To solve this problem, the port system according to the invention makes it possible to fix at least one venous catheter and one arterial catheter, preferably one venous catheter and two arterial catheters, to the umbilical cord in order to avoid unintentional tearing off, also in the case of the infant's movement in the artificial womb chamber. Preferably, part of the port system is located in the amniotic fluid of the artificial womb, which also prevents possible pressure necrosis of the umbilical cord. For this purpose, the port system according to the invention is preferably designed watertight. Preferably, the umbilical vein catheter has a diameter of between 3 and 10 mm, while the catheters for the two umbilical arteries preferably have a diameter of 2 to 7 mm or sizes in between. Preferably, the port system according to the invention is connected to an ECMO device as an oxygenator, wherein oxygenation is preferably realized with donated fetal umbilical cord blood. The transfer of the premature infant takes place by detachment of the natural placenta from the umbilical cord and an immediate embedding into the artificial womb chamber filled with artificial amniotic fluid within the artificial womb system according to the invention. The stent of the port system is preferably located at the end of the tube system in order to avoid unnecessary reduction the diameter of the catheterized vessel, to ensure a secure fixation and also to enable the subsequent fixation of the umbilical cord to the ECMO entrance/exit of the artificial womb system.

Preferably, the catheters of the port system are passed through a holder, which is designed so that it fully encompasses the umbilical cord of the premature infant from the outside. The stent of the port system according to the invention is preferably designed in such a way that the catheters can be connected to the endangium of the umbilical cord. Preferably, the fixation of the port system is realized via the stent via a plurality of small gripping elements or hooks, which engage with the inner wall of the umbilical cord of the premature infant. The associated possibility of developing aseptic pressure necrosis is not critical in this case, since the umbilical cord is cut off at regular intervals, preferably every three to five days, but at the latest after seven days, in the stented area. A re-catheterization of umbilical veins also prevents necrosis and bacterial or viral infection and colonization of the distal end of the umbilical cord. The truncated stump of the umbilical cord can be subjected to a microbiological examination. Due to its length of 60 to 80 cm, the human umbilical cord offers the possibility of easily and efficiently re-catheterizing at regular time intervals, the reduction preferably being between 3 and 5 cm.

Preferably, the port system according to the invention comprises a clamp for fixing the port with the umbilical cord from the outside. In addition to an oxygen supply via the port system according to the invention, which takes place directly via the venous-arterial system of the umbilical cord with simultaneous $CO_2$— seduction, also, in a preferred variant of the womb system, a transcutaneous fetal supply via Carbogen® or oxygen gassing is possible. The Carbogen® gassing involves a gas mixture consisting of about 5 volumes of carbon dioxide ($CO_2$) and 95 volumes of oxygen ($O_2$). Preferably, the oxygenator of the artificial womb directly charges with the Carbogen® gas mixture or oxygen. In an alternative variant, a Carbogen® or $O_2$ treatment is applied to the amniotic fluid of the artificial womb, either before delivery into the chamber of the artificial womb, or by treatment of amniotic fluid, which is already present in the chamber of the artificial womb. The intake of oxygen by the extremely premature infant can therefore be carried out either via the umbilical cord or by transcutaneous supply.

The monitoring of the $O_2$ saturation in the amniotic fluid of the artificial womb is preferably carried out via a measuring device. Furthermore, the measuring device provided according to the invention can also monitor the pressure and/or the temperature, or perform a sonography. The amniotic fluid fed to the artificial womb is preheated by a preheater to a temperature of preferably 37° C. to 39° C. By means of an appropriate heating device, the artificial womb chamber can preferably be kept at a temperature between 37° C. and 38° C.

The artificial womb in a preferred variant comprises connections for ECMO/ECLS tubes, for amniotic fluid inlet and amniotic fluid outlet, for amniotic fluid gassing and/or for urinary diversion. For a successful life support and further development of the premature infant, the composition of the artificial amniotic fluid is crucial as well. Inadequate amniotic fluid composition is liable to cause irreversible damage to fetal internal organs, umbilical cord, amnion, skin, eyes or mucous membranes.

The inventor has also found that fetuses prior to the 28th week of gestation are unable to make use of, to metabolize or to tolerate the commercially offered amino acids (Tchirikov M et al., J. Perinat Med., 2016). The commercial solutions used so far include amino acid concentrations that differ from the physiological conditions in the fetal plasma, sometimes very drastically (in some instances up to 100 times) (Tchirikov M et al., J Perinat Med., 2016). Some amino acids are not even present in commercial preparations. If such an amino acid substitution is performed, no growth occurs in the fetus below 1000 g. Half of these fetuses die within the womb or within one week after delivery.

The amniotic fluid used according to the invention therefore comprises, in a preferred embodiment, a nutrient composition whose concentrations coincide with the physiological situation in the fetus in the respective gestational age. This will ensure that the concentration of fatty acids, vitamins, microelements, growth factors, hormones, electrolytes, cytokines and other regulatory substances is constantly monitored, adapted and substituted if necessary. Preferably, the artificial womb chamber of the artificial womb system according to the invention comprises an artificial amniotic fluid showing the following composition:

|  | Concentration |
| --- | --- |
| Osmolarity [mosm/l] | 240-300 |
| Sodium [mmol/l] | 130-145 |
| Potassium [mmol/l] | 3.5-4.5 |
| Calcium [mmol/l] | 1-2.5 |
| Magnesium [mmol/l] | 0-2 |
| Chloride [mmol/l] | 100-120 |
| Urea [mg/dl] | 0-10 |
| Uric acid [mg/dl] | 0-5 |
| Phosphate [mg/dl] | 0-8 |
| Glucose [mg/dl] | 0-340 |
| Lactate [mmol/l] | 0-20 |
| Citrate [mg/l] | 0-100 |
| Hydrogencarbonate [mmol/l] | 5-100 |
| Total protein [g/l] | 0-10 |
| Albumin [g/dl] | 0-5 |
| Copper [µg/dl] | 0-150 |
| Selenium [µg/dl] | 0-50 |
| Zinc [µg/dl] | 0-30 |
| Total lipids [mg/l] | 0-2000 |
| Phosphatidylcholin (PC) [mg/l] (preferably 80% of total lipids) | 0-1000 |

There are preferably other trace elements included, such as boron, chromium, iron, fluorine, iodine, cobalt, lithium, manganese, molybdenum, nickel, silicon, vanadium, amino acids, growth factors, vitamins and hormones to ensure a physiological development of the premature infant. Preferably, before introducing the amniotic fluid into the artificial womb, it is preheated to a temperature between 37° C. and 39° C. and simultaneously gassed with oxygen or an oxygen-containing gas mixture. Preferably, a container is provided for this purpose, which can hold a pressure of up to 2 bar. For this purpose, preferably pressure gauges are integrated into the wall. Additionally, systems for measuring fetal $O_2$-saturation, ECG electrodes and temperature probes are provided. After cutting the umbilical cord, fetal $O_2$—saturation will be held at 70-80% in the artificial womb system by the oxygenator and/or possibly by gassing of the amniotic fluid. Subsequently, $O_2$-saturation is gradually increased to 89-94%.

In a preferred variant, the womb system also includes at least one access for the provision of additional artificial respiration which could become necessary from the 23./24. week of gestation. The temperature in the artificial womb chamber is preferably kept constant at a temperature between 36° C. and 38° C. by a temperature control device, preferably between 36.5° C. and 37.5° C. The function of body cooling should also be given in case of asphyxia. In a preferred variant, it is provided that the artificial womb chamber is mounted on a movement device. This is intended to reproduce the mother's movement for the fetus. If necessary, a scale may be provided to carry out regular weight measurements of the fetus.

In a further preferred variant, it is provided that maternal sounds are played in the artificial womb via an audio device. The maternal sounds are, for example, the mother's voice, breathing, bowel sounds and heartbeat. These are preferably recorded by the mother by help of a recording device and played to the premature infant in the artificial womb chamber via an audio device. In addition, the mother's voice or sung songs can be played directly during the parents' visit, for which the wall of the artificial womb chamber is preferably made sound permeable. Although the playing of music or sounds to patients is generally known, such variants, however, do not include the playing of maternal sounds, such as breathing, bowel sounds or heartbeat. The aim of the audio exposure according to the invention is to normalize fetal programming and possibly to steer in a positive direction. Also, the production of catabolic stress hormones (for example adrenaline, norepinephrine or cortisone) is supposed to be reduced. In a preferred variant, the combination of different sounds is possible.

Furthermore, the present invention relates to a method for ex vivo treatment of a newborn, preferably an extremely premature infant between the 21/0 and 28/0 WG to maintain its vital functions. Preferably, premature birth is before the completed 28th week of pregnancy. However, the womb system and the procedure according to the invention also work for normal infants, i.e. newborns who have limited life support, for example due to congenital defects or due to not yet developed functions. These include, for example, newborns with a hypoplasia of the lung. These children may be treated with ECMO via the umbilical cord. In this case, it is beneficial that the child and thus the umbilical cord in the womb system according to the invention are embedded in artificial amniotic fluid. This way, the newborn or extremely premature infant suffers no pain, which could be caused by using cannulas or catheterizations.

For this purpose, in a first procedural step, an at least partially ultrasound-permeable chamber with a lumen for receiving amniotic fluid and a neonate, preferably an extremely premature infant before the completed 28th week of gestation, is provided. Subsequently, the newborn or the premature infant is provided with nutrients and oxygen in this womb system. Fetal metabolic waste is eliminated via a dialysis device.

According to the invention, it is now provided that in the lumen of the artificial womb an intraamnial pressure of >0 mbar is maintained, preferably between 2 mbar and 1000 mbar, preferably between 5 mbar and 600 mbar, particularly between 5 mbar and 100 mbar in addition to the atmospheric pressure (1 bar), with all intermediate ranges or intermediate values also being encompassed by the present invention. In a preferred variant, preheated artificial amniotic fluid, preferably 2 l to 20 l per day, is introduced into the artificial womb. In case the lumen is closed, the application of pressure occurs directly in the lumen via various measures (e.g. gassing or fluid supply). In one variant, the lumen may also be open to one side, so that the pressure affects the newborn immediately. Again, the proviso is that the pressure should be >0 mbar in addition to the ambient pressure (atmospheric pressure). The upper limit for treatment is likely to be an absolute pressure of 2 bar, unless certain conditions of the newborn require a higher pressure. In one variant, the intraamnial pressure in the chamber, namely the lumen of the artificial womb is >0 mbar and preferably corresponds to the intraamnial pressure of a natural womb of a living mother.

The inventive method in a preferred variant is characterized in that a port system is provided, which is connected with an oxygenator for the oxygen supply and with the dialysis device. In this case, the port system comprises at least two catheters for connecting the umbilical vein and an umbilical artery as well as a stent connected to the catheters, which is used for anchoring the port system to the umbilical cord.

BRIEF DESCRIPTION OF THE FIGURES

The invention will be explained in more detail in the following figures.

WAYS OF CONSTRUCTING THE INVENTION AND INDUSTRIAL APPLICABILITY

Figure 1:
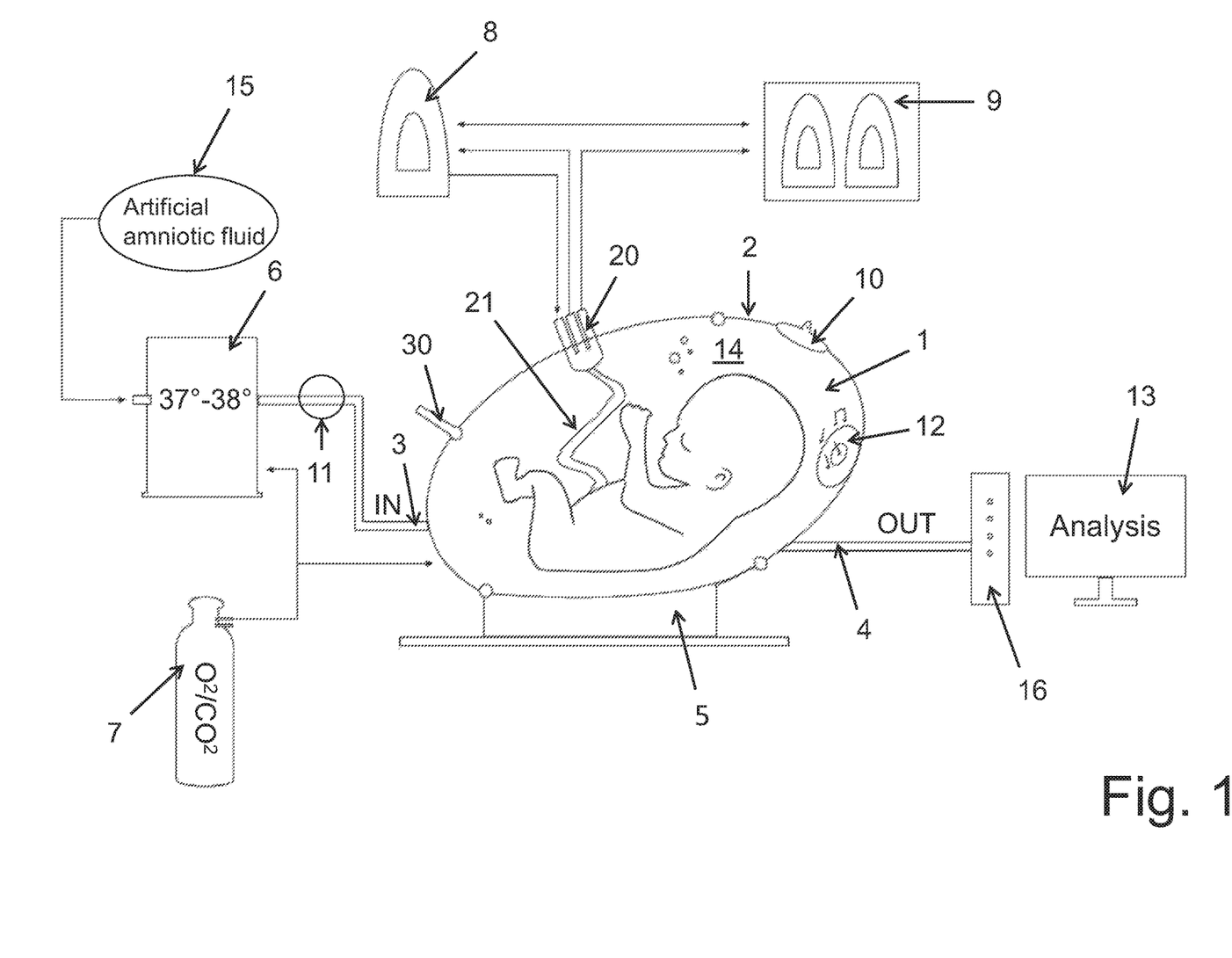
FIG. 1 shows an overview of an embodiment of the artificial womb system according to the invention.

In FIG. 1, the device according to the invention and its individual components are shown. The artificial womb system comprises an artificial chamber 1, said chamber being formed by an at least partly ultrasound-permeable wall 2 of the artificial womb and comprising a lumen 14 for receiving amniotic fluid 15 and a premature infant. The amniotic fluid 15 can be provided, for example, in a reservoir, which preferably has a heating device via which the amniotic fluid 15 can be preheated. Typically, the amniotic fluid 15 is preheated to a temperature between 38° C. and 39° C., with higher temperatures being possible depending on the design of the lines, of the reservoir or of other equipment components. Preferably, the preheating of the amniotic fluid takes place via an amniotic fluid pre-heating device 6, which pre-heats the amniotic fluid 15 feeding chamber 1 of the artificial womb to a temperature of up to 39° C. The amniotic fluid passes through a pump 11 and finally via an access 3 into the chamber 1 of the artificial womb.

A port system 20 according to the present invention connects an umbilical vein and an umbilical cord artery of an umbilical cord 21 with an oxygenator 8. Another umbilical artery is connected to a dialysis device 9. In a preferred variant, the oxygenator 8 and the dialysis device 9 communicate with one another. The oxygenator 8 provides an oxygen supply, if required, with or without a pump. Preferably, ECMO/ECLS equipment is connected. Even using only the port system 20 according to the invention in order to supply the premature infant has led to a significant increase in the survival of the treated fetuses. Preferably, donated umbilical cord blood is used in the ECMO application, which also helps avoiding a lowered Hb level. Also the substitution of nutritional and growth factors can be partially improved via the donated umbilical cord blood.

Preferably, the wall 2 of the chamber 1 of the artificial womb is made of a transparent material, which should have light-subduing and ultrasound-permeable properties. Through an oval opening 10, the artificial womb chamber 1 can be opened from above. Furthermore, the chamber 1 of the artificial womb can be sterilized and the lumen 14 preferably has a volume of 2 to 5 l. Various accesses 30 are provided, for example for connecting ECMO tubes, for gassing amniotic fluid or for nutrient supply. In a preferred variant, the wall 2 of the chamber 1 is double-walled, in order to keep the amniotic liquid at a constant temperature of 37° C. to 38° C.

The artificial womb with chamber 1 of the artificial womb should preferably be able to withstand a pressure of up to 2 bar in case of hypobaric oxygenation (HBO). Usually the intraamnial pressure is between 5 mbar and 100 mbar. If necessary, pressure gauges can be integrated into the wall 2 of the chamber 1 of the artificial womb. For artificial respiration an access 30 is provided from the 23./24. week of gestation. Preferably, in a variant of the womb system, it is provided that in the artificial womb the oxygen supply of the newborn takes place via artificial respiration. The amniotic fluid 15 supplied to the chamber 1 of the artificial womb is preferably infused with a gas mixture 7 (Carbogen® gas mixture) consisting of about 5 volumes of carbon dioxide and 95 volumes of oxygen or with $O_2$. Alternatively, the Carbogen® gas mixture or $O_2$ 7 can also be infused directly into the amniotic fluid 15 of the womb system.

Via a measuring line 4, the sampling for a measuring device 16 can be conducted in order to monitor, for example, the $pO_2$ in the amniotic fluid 15 of the artificial womb chamber 1, the pressure and/or the temperature or the $O_2$-saturation in the premature infant 21. Furthermore, it enables sonography. The analysis of the measurement data of the measuring device 16 is carried out via an analysis device 13. Maternal sounds can be played to the chamber 1 of the artificial womb via an audio device 12.

Figure 2:
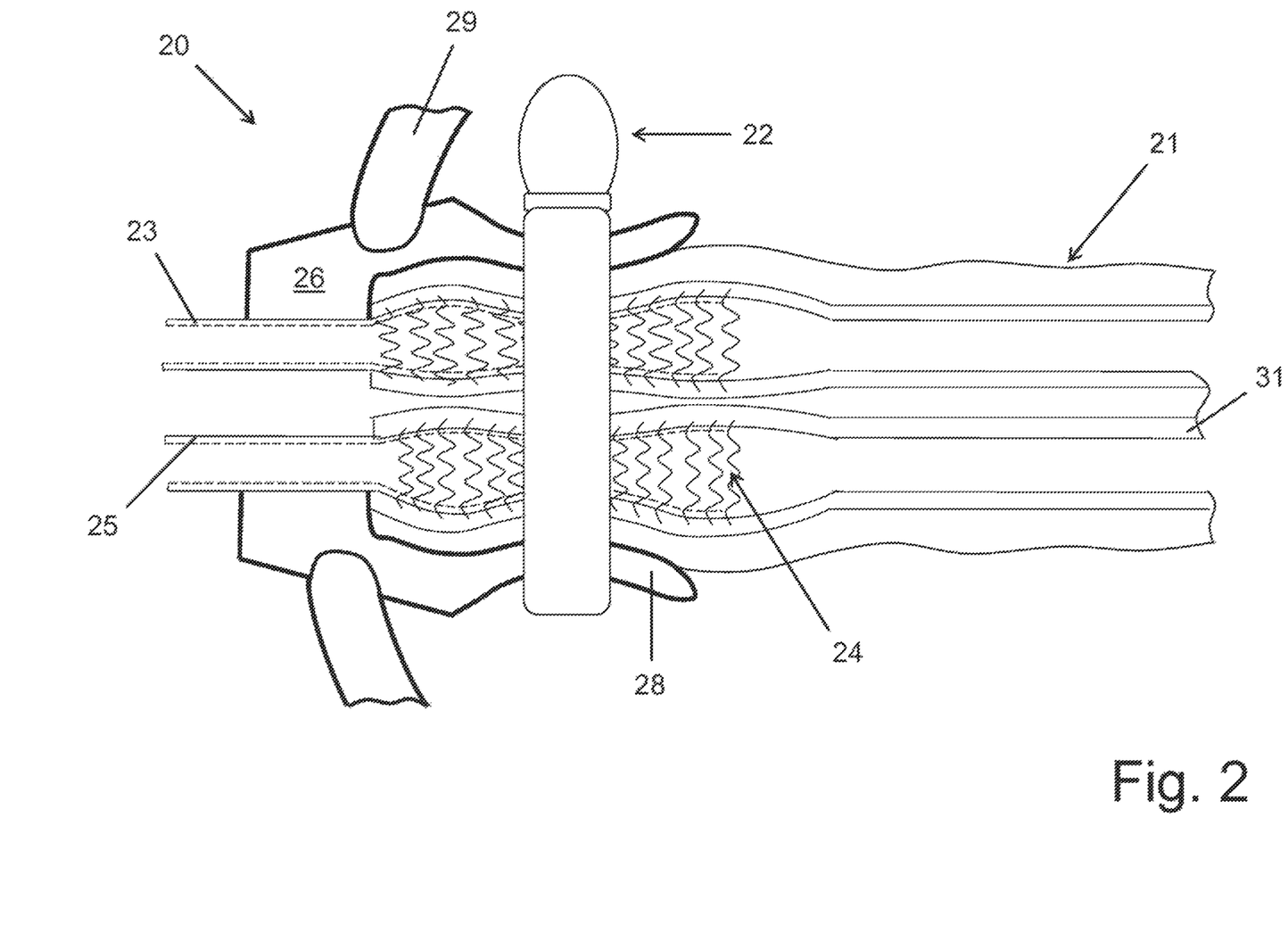
FIG. 2 shows the port system according to the invention.

In FIG. 2, the port system according to the invention is shown in detail. The port system 20 is connected via a holder 26 to the umbilical cord 21 of the premature infant. The holder 26 fully encompasses the outside of the umbilical cord 21. A first catheter 25 is inserted into the umbilical vein. Another catheter 23 is inserted into the umbilical artery. If both umbilical arteries are to be catheterized, the port system 20 according to the invention comprises a first catheter 25 for the umbilical vein and two further catheters 23 for the two umbilical arteries. The umbilical vein and one umbilical artery serve to supply oxygen and are connected to the oxygenator 8. The second umbilical artery is connected to the dialysis device 9 for discharging urine. A premature infant drinks about 250 to 300 ml/kg amniotic fluid, so that the discharging of fetal metabolites (for example bilirubin, $CO_2$) is essential. The umbilical cord 21 and the holder 26 of the port system 20 are held by a clamp 22. The holder 26 preferably comprises a finger-like projection 28 which receives the umbilical cord 21 and the blood vessels integrated therein withstanding the pressing force of the clamp 22. Shown is also a part of the uterine wall 29.

According to the invention, it is provided that the catheters 23, 25 have a stent 24 which, in the variant shown, consists of gripping elements or hooks which grip the endangium of a blood vessel 31 of the umbilical cord 21 with a force fit.

Figure 3:
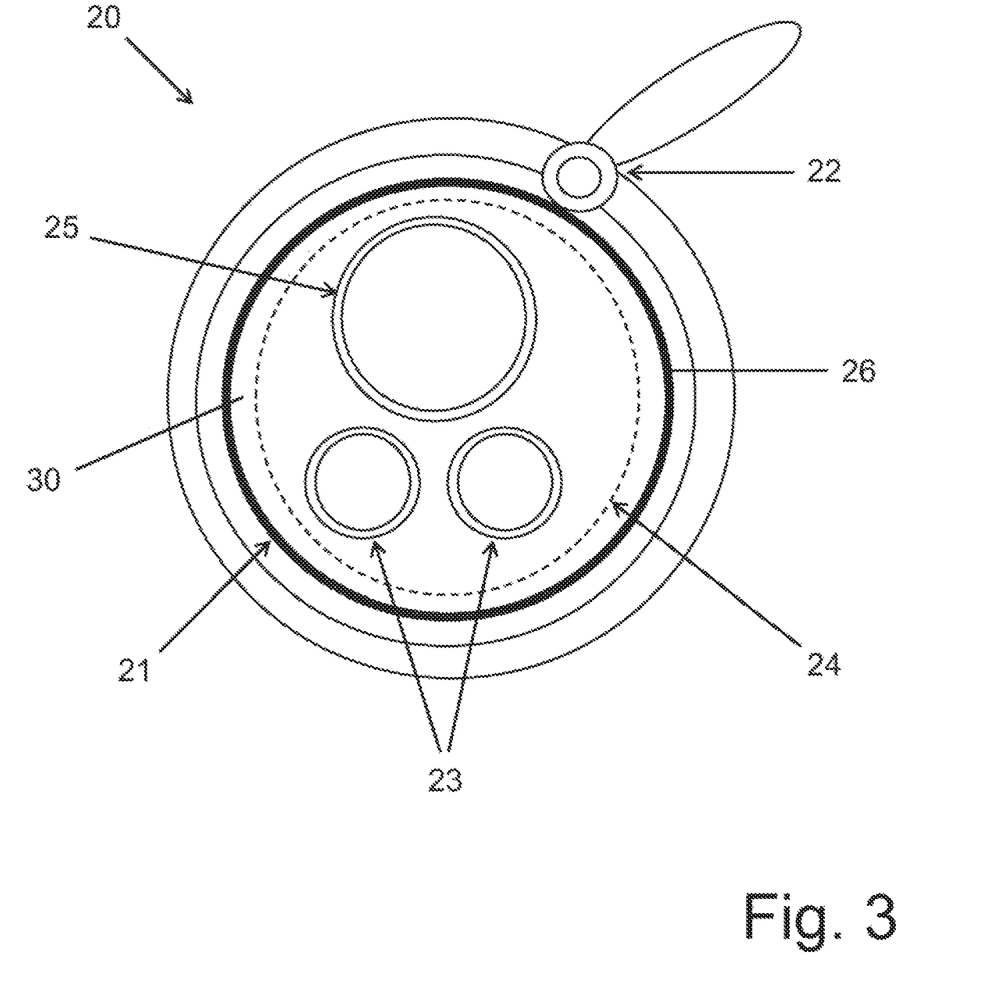
FIG. 3 shows a cross section of a catheterized umbilical cord of a premature infant.

In FIG. 3 a cross section of the port system 20 according to the invention can be seen. It shows the catheter 25 for the umbilical vein and the two catheters 23 for the umbilical arteries. Furthermore, it reveals the stent 24 consisting of a wire mesh which is folded around the catheters 23, 25. The stent 24 fixes the port system 20 to the endangium of the blood vessel 30. An additional clamp 22 ensures the fixation of the port system 20 via the holder 26.

Examples

The artificial womb system according to the invention has been successfully tested in clinical application in the animal model. Herein, the advantages of the port system 20 as well as maintaining the pressure between 5 mbar and 100 mbar in the lumen 14 of the womb system have proved to be particularly advantageous in order to keep the physiological fetal $O_2$-saturation constant, to increase the life expectancy of extremely premature infants and to reduce the morbidity rate. Furthermore, the number of sepsis cases has been significantly reduced, because a catheter replacement of the two catheters 23, 25 by shortening the umbilical cord can be carried out easily and quickly via the port system 20 according to the invention. The respective piece of the umbilical cord 21 is removed during the re-catheterization, so that new catheters 23, 25 can be placed. The umbilical cord 21 is sufficiently long to perform multiple re-catheterizations. Due to the sterile conditions in the artificial womb system, the case of late onset sepsis, which occurs in about 40% of premature infants in the 25th week of gestation (Stoll et al., Trends in Care Practices, Morbidity, and Mortality of Extremely Preterm Neonates, JAMA, 2015) has become manageable.

The womb system according to the invention also allows a quick change of amniotic fluid while maintaining constant temperature and pressure in the womb system. Daily flushing out with 2 to 20 l of amniotic fluid will prevent bacterial and/or Pinz-colonization of the womb system, umbilical cord, fetal skin and mucous membrane. The fetal metabolic waste products, which are excreted via the fetal skin and mucous membrane, can also be removed from the chamber with the artificial amniotic fluid.

An additional gassing of the amniotic fluid can be used to ensure the oxygen supply of the fetal tissue as the fetal skin is extremely thin and gas permeable. If necessary, the $CO_2$ concentration in the mixture can be reduced to a value less than 5%.

In order to be able to permanently guarantee the physiological $O_2$ saturation in premature infants, gassing will take place in the closed womb system under mild hyperbaric conditions of 5 mbar to 100 mbar. Sufficient oxygenation is particularly important for the premature infant during the periodic replacement/renewal of the apparatus and/or of catheter system.

The amniotic fluid supplied to the artificial womb preferably comprises a composition adapted to the stage of development of the premature infant. Amniotic fluid may be used with or without surfactant/glucose. In the variant used, the amniotic fluid comprises the following composition:

Na 143.8 mmol/l, K 3.9 mmol/l, Ca 1.6 mmol/l, Mg 0.57 mmol/l, Cl— 109.5 mmol/l, P 3.3 mg/dl, lactate 9.1 mmol/l, citrate 66.5 mg/dl, HCO 16.9 mmol/l, Cu 16 μm/dl, Se <13.3 μm/dl, Zn 10-24 μm/dl, pH 8.0, osmolarity <271.

Other trace elements such as e.g. boron, chromium, iron, fluorine, iodine, cobalt, lithium, manganese, molybdenum, nickel, silicon and vanadium, amino acids, growth factors, vitamins and hormones may complement the artificial amniotic fluid.

The amniotic fluid is infused with a Carbogen® gas mixture or with $O_2$ in the artificial womb or in a separate container. The temperature was maintained between 37° C. and 39° C., except in the case of body cooling following asphyxia. After 4 to 6 hours, the amniotic fluid is replaced. A complete replacement should take place at the latest after 24 hours in order to avoid infections and colonization. The artificial amniotic fluid pumped through an outlet is used to analyze the kidney function. The amniotic fluid infused with oxygen/Carbogen® can also be used in a continuous regimen of a flush out application of up to 20-30 liters.

The ability to cut the umbilical cord 21 as part of the fixation of the port system 20 according to the invention is an effective method to avoid aseptic pressure necrosis, bacterial and fungal colonization and infections of premature infants. In the clinical trials, a weekly reduction of the umbilical cord length of about 5 cm was performed, without any complications.

The combination of the individual physiological parameters, in particular the connection of an oxygenator 8 with the port system 20 according to the invention, the connection with a dialysis device 9 and the maintenance of a pressure based on the amnial conditions in the chamber of the artificial womb system lead to a significantly improved situation and life support of extremely premature infants.

The invention claimed is:

1. An artificial womb system for supporting newborns or premature infants between 21 and 28 weeks of gestation, comprising:
   a chamber of the artificial womb system, said chamber being formed by an at least partially ultrasound-permeable wall and comprising a lumen for maintaining a physiologically intraamnial pressure and for receiving artificial amniotic fluid and a newborn or a premature infant,
   at least one access configured for supplying the newborn or premature infant in the artificial womb system with nutrients,
   an oxygenator and/or a gassing device for supplying oxygen to the newborn or premature infant,
   a dialysis device, wherein the oxygenator and the dialysis device are connected to a port system which is configured to be connected to an umbilical cord of the newborn or premature infant, said port system comprising:
   at least two catheters configured for connecting to an umbilical vein and at least one umbilical cord artery of the newborn or premature infant, and
   a stent, which is connected to the at least two catheters for fixing the port system to the umbilical cord,
   said artificial womb system configured to maintain an intraamnial pressure of >0 mbar in addition to the atmospheric pressure acting on the newborn or premature infant in the chamber of the artificial womb system, and to apply an oxygen containing gas mixture or $O_2$ treatment to the artificial amniotic fluid of the artificial womb system, either before delivery into the chamber of the artificial womb system, or by treatment of amniotic fluid, which is already present in the chamber of the artificial womb system.

2. The artificial womb system according to claim 1, further comprising a pump which feeds amniotic fluid and/or oxygen containing gas mixture or oxygen into the chamber of the artificial womb system to maintain an intraamnial pressure of >0 mbar, in addition to the atmospheric pressure.

3. The artificial womb system according to claim 2, wherein the intraamnial pressure is between 5 mbar and 1000 mbar.

4. The artificial womb system according to claim 1, characterized in that the at least two catheters of the port system are guided by a holder designed to fully encompass the umbilical cord of the newborn or premature infant from outside and characterized in that the stent connected to the at least two catheters is designed in such a way that the at least two catheters can be connected to the endangium of a blood vessel of the umbilical cord.

5. The artificial womb system according to claim 1, characterized in that the stent comprises a number of fasteners for fixing the port system via the endangium of a blood vessel.

6. The artificial womb system according to claim 1, further comprising a temperature control device in order to maintain a constant temperature between 36.5° C. and 37.5° C. in the chamber of the artificial womb system.

7. The artificial womb system according to claim 1, wherein maintaining an intraamnial pressure of >0 mbar, in addition to the atmospheric pressure in the chamber is done by gassing and/or amniotic fluid, acting on the newborn or premature infant in the chamber.

8. The artificial womb system according to claim 1, characterized in that the system provides accesses for ECMO/ECLS tubes, for amniotic fluid inlet and amniotic fluid outlet, for amniotic fluid gassing and/or for the discharge of metabolic waste and urine of the newborn or premature infant.

9. The artificial womb system according to claim 1, characterized in that the chamber of the artificial womb system comprises artificial amniotic fluid, which has the following composition:

|  | Concentration |
|---|---|
| Osmolarity [mosm/l] | 240-300 |
| Sodium [mmol/l] | 130-145 |
| Potassium [mmol/l] | 3.5-4.5 |
| Calcium [mmol/l] | 1-2.5 |
| Magnesium [mmol/l] | 0-2 |
| Chloride [mmol/l] | 100-120 |
| Urea [mg/dl] | 0-10 |
| Uric acid [mg/dl] | 0-5 |
| Phosphate [mg/dl] | 0-8 |
| Glucose [mg/dl] | 0-340 |
| Lactate [mmol/l] | 0-20 |
| Citrate [mg/l] | 0-100 |
| Hydrogencarbonate [mmol/l] | 5-100 |
| Total protein [g/l] | 0-10 |
| Albumin [g/l] | 0-5 |
| Copper [µg/dl] | 0-150 |
| Selenium [µg/dl] | 0-50 |
| Zinc [µg/dl] | 0-30 |
| Total lipids [mg/l] | 0-2000 |
| Phosphatidylcholin (PC) [mg/l] | 0-1000. |

10. The artificial womb system according to claim 1, characterized in that the oxygenator infuses the chamber of the artificial womb system or the amniotic fluid led into the chamber with a gas mixture consisting of about 5 volumes of carbon dioxide ($CO_2$) and 95 volumes of oxygen $O_2$, or with $O_2$ only.

11. The artificial womb system according to claim 1, further comprising a measuring device for monitoring $O_2$, saturation in the newborn or premature infant, in the amniotic fluid of the system, the pressure and/or the temperature in the chamber of the artificial womb system or for performing sonography.

12. The artificial womb system according to claim 1, further comprising an amniotic fluid pre-heating device which may pre-heat the amniotic fluid to a temperature of up to 39° C. before entering the chamber.

13. The artificial womb system according to claim 1, characterized in that the artificial womb system is mounted on a moving device and/or scale.

14. The artificial womb system according to claim 1, wherein said artificial amniotic fluid further comprises boron, chromium, iron, fluorine, iodine, cobalt, lithium, manganese, molybdenum, nickel, silicon, vanadium, amino acids, growth factors, vitamins and/or hormones.

15. A method of treatment of a neonate or premature infant between 21 and 28 weeks of gestation, to maintain its vital functions, comprising the steps providing an at least partially ultrasound-permeable chamber of an artificial womb with a lumen for receiving amniotic fluid and the neonate or premature infant, and a port system connected to an oxygenator and/or gassing agent for oxygen supply and to a dialysis device, wherein the port system comprises at least two catheters for connecting an umbilical vein and an umbilical artery and a stent, which serves to anchor the port system to an umbilical cord, supplying the neonate or premature infant in the chamber of the artificial womb with nutrients and oxygen via an oxygenator and/or a gassing device, characterized in that an intraamnial pressure >0 mbar in addition to atmospheric pressure acting on the neonate or premature infant is maintained in the artificial womb, an oxygen containing gas mixture or $O_2$ treatment is applied to the amniotic fluid of the artificial womb, either before delivery into the chamber of the artificial womb, or by treatment of amniotic fluid, which is already present in the chamber of the artificial womb.

16. The method according to claim 15, characterized in that maternal sounds, heartbeat, bowel sounds, breathing sounds and voice are played via an audio device to the artificial womb.

17. The method according to claim 15, characterized that metabolic waste products are discharged via a dialysis device.

18. The method according to claim 15, characterize in that metabolic waste products are flushed with artificial amniotic fluid.

* * * * *